United States Patent [19]
Baran

[11] Patent Number: 5,617,874
[45] Date of Patent: Apr. 8, 1997

[54] AUTOMATED BIOPSY INSTRUMENT

[76] Inventor: Gregory W. Baran, 8160 Belle Vernon Rd., Novelty, Ohio 44072

[21] Appl. No.: 349,936

[22] Filed: Dec. 6, 1994

Related U.S. Application Data

[63] Continuation-in-part of Ser. No. 52,788, Apr. 23, 1993, Pat. No. 5,400,798, which is a continuation-in-part of Ser. No. 905,832, May 29, 1992, abandoned, which is a continuation of Ser. No. 686,785, Apr. 17, 1991, Pat. No. 5,125,413, which is a continuation of Ser. No. 330,230, Mar. 29, 1989, Pat. No. 5,025,797.

[51] Int. Cl.$^6$ ........................ A61B 10/00
[52] U.S. Cl. ........................ 128/753
[58] Field of Search ............... 128/751–754; 606/167

[56] References Cited

U.S. PATENT DOCUMENTS

| | | | |
|---|---|---|---|
| 4,476,864 | 10/1984 | Tezel | 128/754 |
| 4,570,632 | 2/1986 | Woods | 128/751 |
| 4,600,014 | 7/1986 | Beraha | 128/754 |
| 4,699,154 | 10/1987 | Lindgren | 128/754 |
| 4,735,215 | 4/1988 | Goto et al. | 128/754 |
| 4,881,551 | 11/1989 | Taylor | 128/754 |
| 5,047,008 | 9/1991 | de Juan et al. | 128/751 |
| 5,090,419 | 2/1992 | Palestrant | 128/754 |
| 5,172,701 | 12/1992 | Leigh | 128/753 |
| 5,172,702 | 12/1992 | Leigh et al. | 128/754 |
| 5,183,052 | 2/1993 | Terwilliger | 128/753 |
| 5,213,110 | 5/1993 | Kedem et al. | 128/754 |
| 5,282,476 | 2/1994 | Terwilliger | 128/753 |

FOREIGN PATENT DOCUMENTS 141108 2/1901 Germany.

OTHER PUBLICATIONS

Kenneth D. Hopper, MD, Steve H. Parker, MD, and Wayne F. Yakes, MD, "The Biopsy Gun," Hospimedica, Nov., 1991, pp. 52–55.

*Primary Examiner*—Max Hindenburg
*Attorney, Agent, or Firm*—Varnum, Riddering, Schmidt & Howlett LLP

[57] ABSTRACT

The invention is for a biopsy instrument having a stationary shaft secured to which is a stylet such that, once secured, the stylet does not move relative to the instrument. The stylet is telescopically received by a cannula which is mounted to a spring-loaded guide; the cannula and the guide move between charged and discharged positions. Also provided is a safety cap, which travels within slots formed in opposite sides of the cylindrical casing that houses the shaft, the guide and the spring. Retracting the safety cap moves the guide and the cannula from the discharged to the charged position where a release lever engages the guide. The safety cap covers the release lever to prevent accidental actuation of the instrument. The instrument is fired by sliding the safety cap forward and depressing the exposed release lever, which allows the spring to drive the cannula forward, toward the discharged position and over the stationary stylet, so that a tissue sample may be taken. Further, the biopsy instrument has a sealed chamber disposed behind the cannula. The sealed chamber creates a vacuum when the biopsy instrument is discharged. The vacuum aids in retaining the tissue sample within the cannula.

18 Claims, 10 Drawing Sheets

AUTOMATED BIOPSY INSTRUMENT

This application is a continuation-in-part of application Ser. No. 08/052,788, filed Apr. 23, 1993, now U.S. Pat. No. 5,400,798, issued Mar. 28, 1995, which is a continuation-in-part of application Ser. No. 905,832, filed May 29, 1992, now abandoned, which is a continuation of application Ser. No. 685,785, filed Apr. 17, 1991, from which issued U.S. Pat. No. 5,125,413 on Jun. 30, 1992, which is a continuation of application Ser. No. 330,230, filed Mar. 29, 1989, from which issued U.S. Pat. No. 5,025,797 on Jun. 25, 1991.

BACKGROUND OF THE INVENTION

1. Field of the Invention

This invention relates generally to a biopsy instrument; viz., a device for removing a sample of tissue from a human being or an animal. More particularly, the invention relates to an automated biopsy instrument in which a spring-loaded outer cannula is driven over an inner stationary stylet to obtain the tissue sample.

2. Description of the Related Art

The procedure known as biopsy, or the removal of samples of human and animal internal tissue, has been for many years a favored method for the nonsurgical diagnosis of tissue. Traditionally, biopsy has been performed in a two-step manual technique employing a needle in which an outer hollow cutting cannula telescopically receives an inner stylet which is slidable between retracted and extended positions relative to the cannula. In performing the first step of the technique, the physician places the tip of the needle (with the stylet retracted inside the cannula) against the tissue mass to be sampled and manually drives the stylet forward into the tissue mass. In a typical instrument of this type, the styler extends rearwardly therefrom and is fitted with a push-knob to facilitate the driving of the styler in the forward direction. To carry out the second step, the physician manually drives the cutting cannula forwardly over the stylet, thereby severing a tissue sample and retaining it within the cannula's hollow interior. This procedure produces what is referred to as a core biopsy specimen.

Examples of manually operated biopsy needles of this general type are disclosed in U.S. Pat. No. 4,600,014, issued Jul. 15, 1986 to D. Beraha for "Transrectal Prostate Biopsy Device and Method", and U.S. Pat. No. 3,477,423, issued Nov. 11, 1969 to L. K. Griffith for "Biopsy Instrument".

Such manually operated two-step devices are awkward to manipulate, and the tissue samples obtained may often be unsatisfactory. The depths to which the stylet and the cannula are driven into the tissue mass must be carefully controlled for accuracy and efficiency. Caution is required, as well, in applying the force with which the stylet and cannula are plunged forward. Too little force may not sever the tissue sample from the mass; too much force may cause unnecessary damage to the surrounding vital tissues.

In an effort to remedy these problems, various automated devices have been developed. For example, U.S. Pat. No. 3,452,741, issued Jul. 1, 1969 to R. C. Schaffer for "Conetome", discloses an instrument for performing cervical biopsies in which an electric motor imparts reciprocating movement to a pair of serrated scalpel blades.

U.S. Pat. No. 4,667,684, issued May 26, 1987 to H. G. Leigh for "Biopsy Device", discloses a movable stylet telescopically received in a hollow movable cannula, both the stylet and the cannula being mounted to hubs within a pistol-style grip. In use, the stylet is first manually advanced into the tissue and the cannula is then driven over the stylet by depressing a trigger.

U.S. Pat. No. 4,699,154, issued Oct. 13, 1987 to one Lindgren for "Tissue Sampling Device", discloses a complicated biasing mechanism in which a release button is depressed to cause a spring-loaded stylet to be advanced into the tissue mass. The forward movement of the stylet also triggers the delayed release of a spring-loaded outer cannula, which slides over the styler to sever the tissue sample.

The aforementioned U.S. Pat. No. 4,600,014 to Beraha discloses an embodiment in which, after a slidable stylet is manually advanced into the tissue mass, a spring-loaded outer cannula is released and driven over the stylet to sever the tissue sample.

Several prior automated biopsy instruments employ a stylet formed with an elongated transverse slot or notch adjacent to its sharpened tip. This slot provides a pocket in which is captured a severed tissue sample when the cannula is driven forward over the stylet in the second step of the biopsy procedure. Typical of this form of stylet is the TRU-CUT® Needle marketed by Travenol Laboratories, Inc., Deerfield, Illinois.

An important feature of another known device, The Roth Biopsy Needle, marketed by Cook Urological, Inc., Spencer, Indiana, is a stylet which is manually adjustable between extended and retracted positions for reasons which will be apparent from the following description of its various methods of operation. The stylet is loaded from the rear of the instrument and extends behind the instrument at all times. The stylet is mounted to a U-shaped handle which is engageable with the body of the instrument in two positions corresponding to the extended and retracted stylet positions. A spring-loaded cannula is also movable between a charged or rear position and a discharged or advanced position.

In one method of using the Roth needle, the physician first adjusts the stylet manually to its retracted position and moves the cannula manually to the charged position to expose the sharpened tip of the stylet. He then penetrates the tissue mass with the stylet and depresses a button-release to cause the cannula to be driven by the spring forwardly over the tip of the stylet to sever the tissue sample and retain it within the hollow tip of the cannula. It is to be borne in mind that the stylet of the Roth needle is movable, as mentioned above, and that the button-release is exposed at all times and therefore subject to inadvertent actuation. It should also be noted that because the stylet and the associated U-shaped handle extend behind the instrument, the stylet and handle are always exposed and are therefore vulnerable to accidental impact or unintended forces, thereby creating a risk that the stylet may be inadvertently advanced into the body of the patient with possibly deleterious consequences.

In another method of using the Roth needle, the physician proceeds as before, but after penetrating the tissue mass he manually advances the stylet to its extended position to expose the transverse slot or gap therein described above. When the cannula is advanced, the tissue sample is severed and captured in the pocket formed by the slot.

In an alternative variation of the foregoing method, the physician may begin the procedure with the stylet in the extended position and the cannula in the discharged mode. Once the tissue has been penetrated, the cannula is manually retracted to expose the transverse slot. However, it is to be noted that all stylets formed with such a tissue pocket, whether employed in the Roth needle or in other biopsy instruments, become unstable when tooled to gauge sizes larger than 20 gauge (i.e., 21, 25 gauge). At higher gauge numbers (i.e., smaller diameter stylets) the bridge joining the stylet's proximal and distal ends at the tissue pocket becomes increasingly flexible, and therefore the stylet becomes physically unstable and its direction impossible to control with any precision when the slot or gap is exposed during penetration of the tissue mass by the stylet. Moreover, certain areas of the body such as the pancreas, thyroid, and nonpleural-based intrapulmonary lesions are routinely biopsied with needles smaller than 20 gauge (i.e., 21 gauge) to reduce the incidence of hemorrhage and pneumothorax.

In any event, the various automated biopsy instruments presently known tend to be heavy, difficult to manipulate, and incorporate biasing mechanisms which are either complicated in construction or require undue force to operate. Such limitations diminish the physician's control over the instrument and the precision with which biopsies may be performed. These instruments may be subject to inadvertent movement or torque which may, in turn, subject the patient to unnecessary trauma and risk. This is especially true of instruments which permit or require adjustment of the relative positions of any of their elements before the cannula is moved forward to sever the tissue sample. Similarly, the length of time required to perform a biopsy increases as the physician's degree of control of the instrument decreases, further elevating the risk to which the patient may be exposed. Finally, both physician and patient are exposed to the risk of inadvertent advancement of the cannula when the instrument is in its charged condition.

SUMMARY OF THE INVENTION

The present invention provides an apparatus for acquiring a biopsy specimen comprising a biopsy actuator having a casing. An outer cannula is adapted to mount the biopsy actuator for movement with respect to the casing. The cannula has a predetermined inner diameter with a distal end and a proximal end. The distal end is inserted into the tissue of the patient and its proximal end is attached to the biopsy actuator. The biopsy actuator further comprises a stylet means which has an outer diameter commensurate with the inner diameter of the cannula. The stylet means is adapted for insertion into the proximal end of the cannula and is detachable therefrom. When the stylet means is inserted into the cannula, the stylet means closes the distal end of the cannula during insertion of the cannula into the patient's body. The body actuator further includes means for rapidly advancing the distal end of the outer cannula beyond the distal end of the stylet means to acquire a biopsy specimen. The biopsy actuator also includes a sealed chamber in fluid communication with the cannula for creating a low-pressure area in the sealed chamber in the cannula when the cannula is advanced during the acquisition of the biopsy specimen. The biopsy actuator has a coupling adapted to couple the sealed chamber to a low-pressure device.

In another aspect of the invention, the biopsy actuator further comprises a stylet support and a cannula support, which define the sealed chamber. A substantially fluid-tight seal is positioned between the stylet support and the cannula support. Preferably, the substantially fluid-tight seal is an elastomeric sealing member, such as an elastomeric cap and retainer, an elastomeric O-ring, or an elastomeric sleeve.

In yet another aspect of the invention, the stylet support is a hollow rod, which defines a channel extending therethrough and one of the channel forms a coupling and the other end of the channel is fluidly connected to the sealed chamber. Preferably, one or more access openings fluidly connect the channel to the sealed chamber. The access openings extend from the channel to the side of the stylet support. Alternatively, the access openings can extend from the channel to the end of the stylet support. The stylet support can have a clevis at the other end of the stylet support for mounting the stylet and the at least one access opening is disposed away from the clevis. Preferably, the stylet support further comprises an end plate mounted to one end of the stylet support and sized to close an end of the casing. The end plate can form the coupling, which is preferably a hose having one end press-fit within the channel and the other end adapted to mount to the low-pressure device.

DETAILED DESCRIPTION OF THE INVENTION

Figure 1:
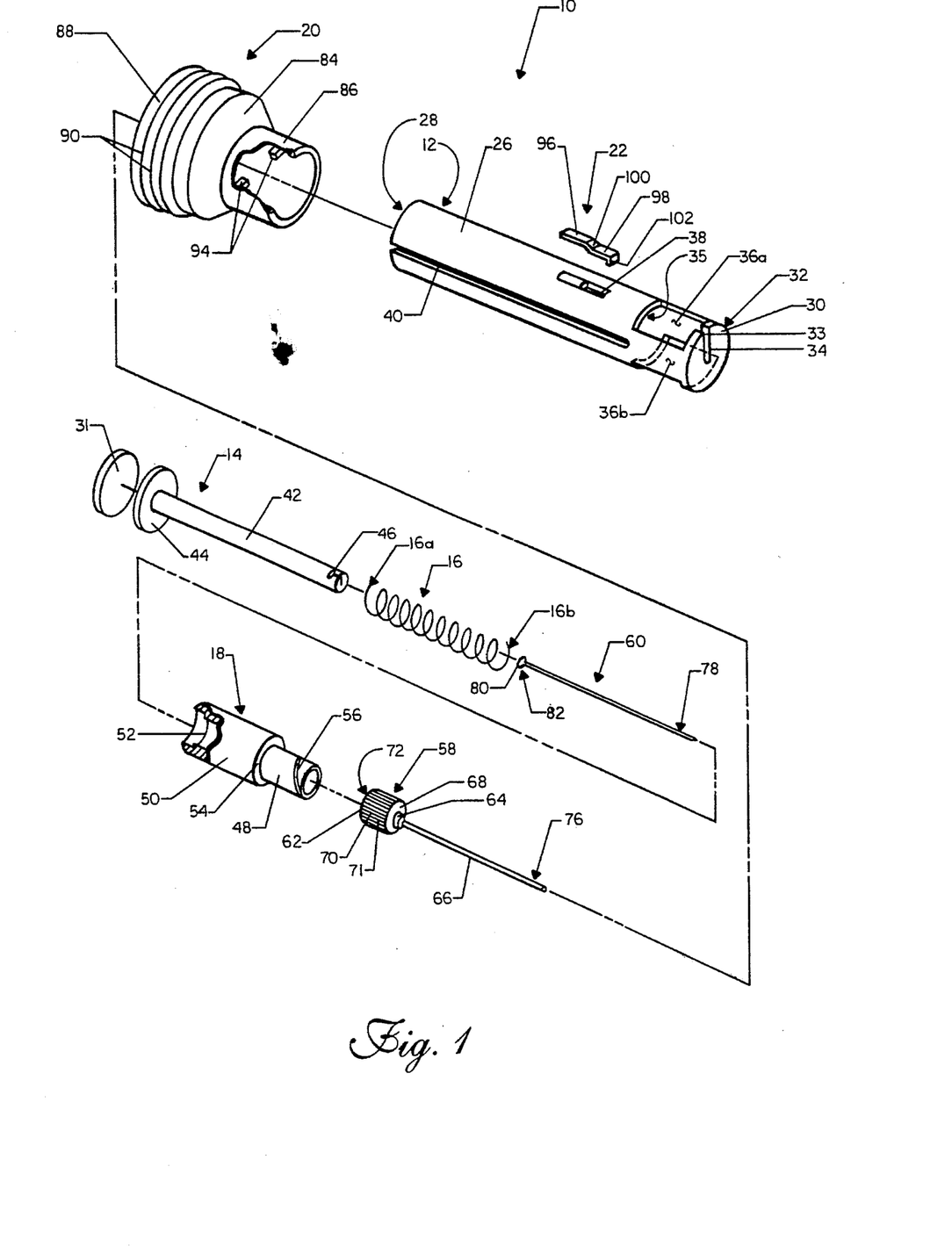
FIG. 1 is an exploded perspective view of the major components of a biopsy instrument comprising an embodiment of the invention.
Figure 1A:
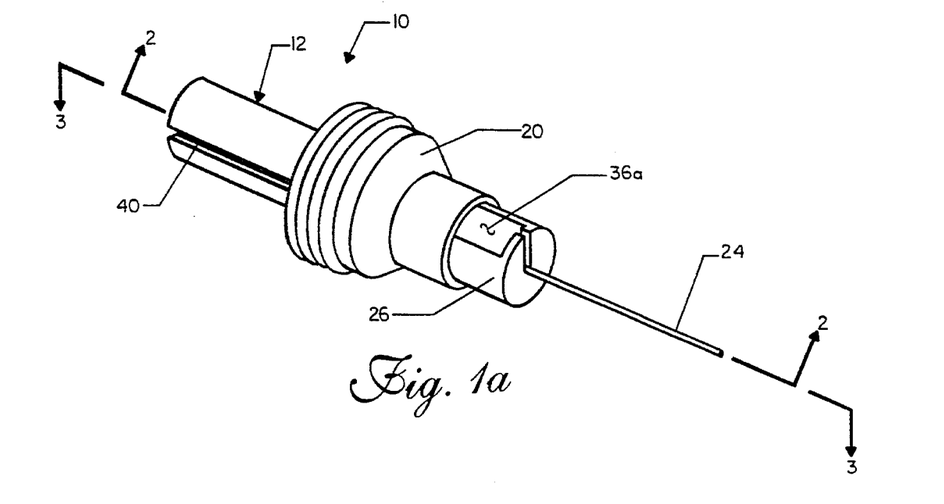
FIG. 1A is a perspective view of the biopsy instrument of FIG. 1 in a fully assembled condition.

Referring now to the drawings, and particularly to FIGS. 1 and 1A, an automated biopsy instrument according to the invention is designated generally by the reference numeral 10. The instrument 10 comprises seven principal elements, which will be more fully described hereinbelow: an outer casing 12; an inner support rod 14; a coil spring 16; a biopsy spring guide 18; a safety cap 20; a release lever 22; and a needle 24.

The outer casing 12 comprises an elongated hollow cylindrical tube 26 open at a rear end 28 thereof and substantially closed by an end wall 30 which is formed integrally with the tube 26 at the opposite or forward end 32 thereof. The open end 28 is closed by a cap 31. A cannula slot 34 in the end wall 30 communicates with a hollow interior 35 of the tube 26. The slot 34 extends radially from a center point of the end wall 30 to the periphery thereof. A cone-shaped depression 34a is formed in the interior face of the end wall 30 at the closed end of the slot 34, the broader end of the depression 34a opening toward the interior 35 of the tube 26.

Provided in the tube 26 at the forward end 32 thereof, and spaced from the end wall 30, are a pair of substantially rectangular access ports 36a and 36b which communicate with the hollow interior 35 of the tube 26. Access port 36a circumscribes an arc of approximately 90 degrees about the circumference of the outer casing 12, communicates with the cannula slot 34 at an intersection designated by the reference character 33, and extends symmetrically in either direction from the intersection 33. Access port 36b is diametrically opposite from port 36a and is identical therewith except that it does not communicate with the cannula slot 34.

The outer casing 12 includes a release lever seat 38 provided by a rectangular aperture which is formed in the tube 26 and communicates with the interior 35 thereof. Seat 38 is positioned approximately at the longitudinally central portion of the tube 26 and in line with the cannula slot 34.

The outer casing 12 is additionally provided with a pair of longitudinal guide slots 40 which are formed in the tube 26 and extend from the rear end 28 thereof toward the opposite or forward end 32. The guide slots 40 are disposed diametrically oppositely from one another and approximately midway between, or 90 degrees from, the access ports 36a, 36b.

The internal support rod 14 comprises an elongated solid cylindrical shaft 42 joined to a circular or disc-shaped base 44. An anchor socket or clevis 46 is formed in the distal end of the shaft.

The biopsy spring guide 18 is hollow and open at its opposite ends and comprises a forward cylinder 48 and a rear cylinder 50 joined coaxially therewith. The outside diameter of the forward cylinder 48 is smaller than that of the rear cylinder 50, the forward cylinder 48 communicating with and extending from the rear cylinder 50. An annular internal shoulder 52 is formed in the rear cylinder 50. The walls of the two cylinders are continuous, thereby forming an annular external shoulder 54. The exterior surface of the distal end of the forward cylinder is formed with a quarter-turn male thread 56.

Figure 2:
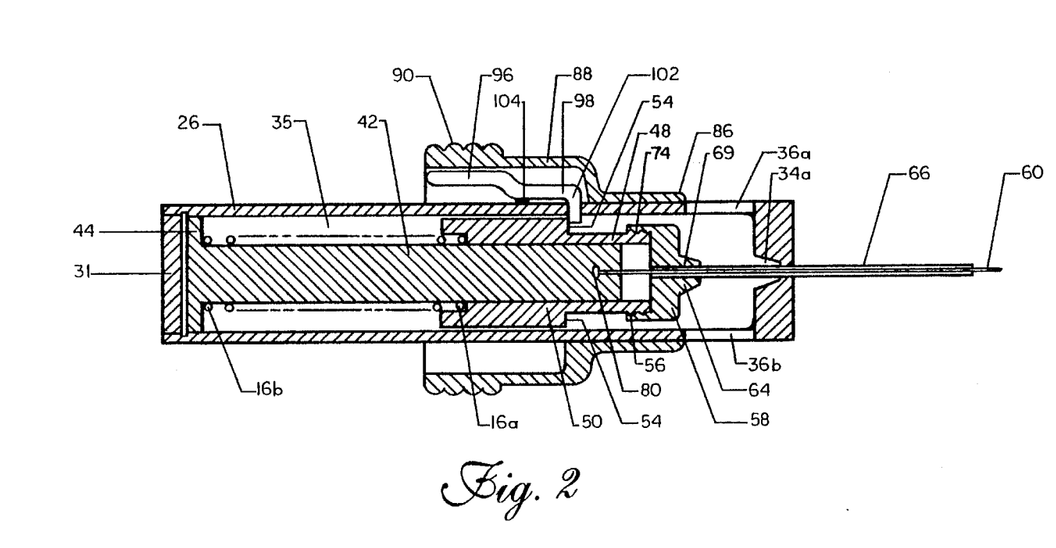
FIG. 2 is a longitudinal sectional view taken along line 2—2 of FIG. 1A and showing the biopsy instrument of FIGS. 1 and 1A in a "charged-safety-on" mode.

The needle 24 comprises a cannula mount 58 and a stylet 60. The cannula mount 58, in turn, comprises a cylindrical collar 62, a conical head 64, and a cutting cannula 66. The collar 62 is open at one end thereof and is closed at its opposite end by an end wall 68 pierced by a centrally disposed, narrow axial bore 69 (FIG. 2). An outer surface 70 of the collar 62 is provided with knurling 71 for improved grip, while an inner surface 72 is formed with a quarter-turn female thread 74 adapted to mate with the thread 56 of spring guide 18. The conical head 64 is secured to the end wall 68 over the axial bore 69, and is itself axially bored to communicate with the interior of the cylindrical collar 62 by way of bore 69, whereby the cutting cannula 66 is received by the head 64 and end wall 68 and is there secured in any suitable manner. The cutting cannula 66 comprises a hollow tube which is beveled to an appropriate angle at its distal end 76 (the particular angle depending on the style of cannula employed) and sharpened about its circumference at the distal end 76.

It will be noted at this point that the hollow interior of the cannula is in communication with the interior of collar 62.

Although the cutting cannula 66 is described as being of a certain configuration, it is not so limited. Because the cannula mount 58 is detachably affixed to the spring guide 18, the biopsy instrument 10 may interchangeably employ a needle having any one of several configurations well known in the art, including but not limited to those variously known by or marketed under the names Turner, Chiba, Franseen, Tip-cut, Menghini, and Bernardino/Sones. The biopsy instrument 10 may also employ a TRU-CUT needle, as discussed more fully hereinafter.

The stylet 60 is sharpened to a point at its distal end 78 and is formed with an anchor 80 at its proximal end 82. It will be apparent that the stylet need not be formed with a tissue pocket or sampling gap; that is, a transverse slot located adjacent to the sharpened distal end 78, as will be discussed with greater particularity hereinafter.

The safety cap 20 or shield means is a roughly bell-shaped hollow element open at both ends and surrounding the cylindrical tube 26. A web 84 thereof joins a narrow, hollow cylindrical forward section 86 to a hollow cylindrical rear section 88 of greater diameter than the forward section 86. The rear section 88 is formed with a series of circumferential ribs 90 for improved grip, and it will be noted that configuration of the safety cap 20 is such that it may be encirclingly engaged or grasped by the thumb and fingers of one hand. Integrally formed on an interior surface 92 of the forward section 86 of the safety cap, at a point where the forward section 86 and the web 84 merge, are a pair of oppositely disposed, elongated guide pins 94 of square cross section.

The release lever 22 comprises a finger rest 96 and a mounting section 98 maintained in spaced parallel planes by a connecting web 100. The finger contacting surface of the finger rest 96 may be appropriately textured for improved grip. Mounting section 98 is formed with a latching projection 102 at one end of the release lever and is flexibly secured to the outer casing 12 by a spot weld 104 (FIG. 2).

In assembly, a biasing means in the form of the coil spring 16 is coaxially received over the cylindrical shaft 42 of the internal support rod 14 with a first end 16a of the spring bearing against the base 44 to which the shaft 42 is mounted. The rod 14 and the spring 16 are in turn telescopically received within the biopsy spring guide 18 with a second or opposite end 16b of the spring 16 bearing against the internal shoulder 52 of the spring guide.

Next, the support rod 14, the coil spring 16, and the spring guide 18 are telescopically received within the outer casing 12, and the subassembly so formed is then received within the safety cap 20 with the guide pins 94 thereof registering with the guide slots 40 in the outer casing 12. The safety cap 20 is slidable over the outer casing 12, the extent of forward movement thereof being limited by the length of the guide slots 40. The rear end 28 of the tube 26 is closed by the cap 31.

The stylet 60 is telescopically or coaxially received within the cannula mount 58 to assemble the needle 24. The needle is then positioned within the hollow interior 35 of the tube 26 with the collar 62 of the cannula mount 58 aligned with the access ports 36a, 36b and the cannula 66 resting in the cannula slot 34. In this position, the anchor 80 of the stylet 60 is received and detachably engaged within the clevis 46 of the spring guide 18. The thread 74 on the inner surface 72 of the collar 62 is engaged with the thread 56 on the spring guide 18 to secure the cannula mount 58 to the spring guide.

The fully assembled biopsy instrument 10 has three operating modes: namely, the discharged mode, the charged-safety-on mode, and the charged-ready mode. In the discharged mode, best shown in FIG. 4A, the safety cap 20 is positioned approximately at the forward end 32 of the tube 26 so that the forward section 84 of the safety cap covers the access ports 36a, 36b. The spring guide 18 is disposed at the forward end 32 of the tube 26 with the head 64 of the cannula mount 58 resting within the complementary cone-shaped depression 34a.

Figure 3:
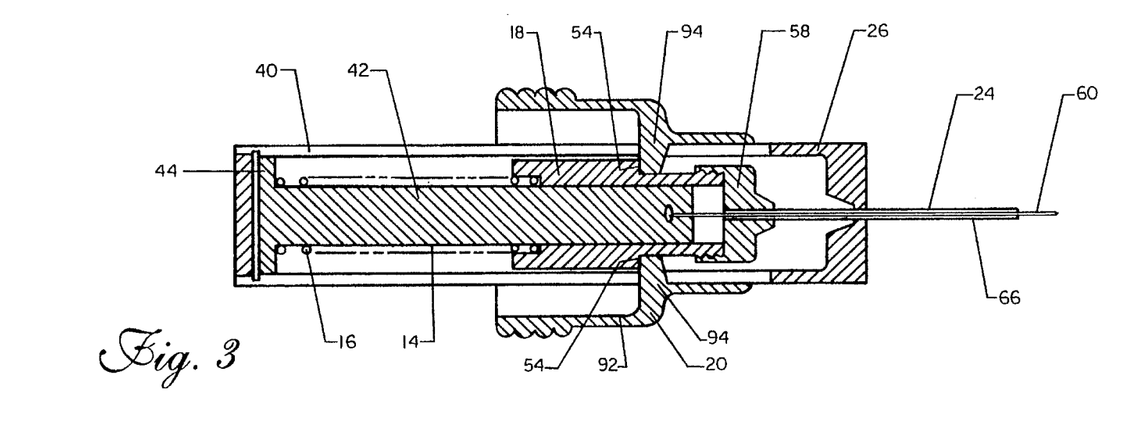
FIG. 3 is a longitudinal sectional view of the biopsy instrument of FIGS. 1, 1A and 2, taken along line 3—3 of FIG. 1A.

The instrument 10 may be converted from the discharged mode to the charged-safety-on mode, best shown in FIG. 2, by retracting the safety cap 20 toward the rear end 28 of the tube 26. The configuration of the safety cap permits this to be done with equitable distribution of the retracting force applied by the hand of the physician: that is, unlike examples of the prior art, the retracting force is not concentrated at the tip of the thumb or one or two fingers. This action causes the guide pins 94 (FIG. 3) to engage the annular external shoulder 54 of the spring guide 18 to retract the spring guide toward the base 44 of the support rod 14 and compress the coil spring 16. Thus, an easy functioning, manually operated charging means has been provided. At the same time, and by this action, the cannula 66 is retracted to expose the distal end portion of the stylet 60. However, it is important to note that a stationary means for mounting the stylet on the instrument 10 in fixed relation thereto has been provided; both the stylet 60 and the support rod 14 remain stationary. The safety cap 20 and the spring guide 18 are retracted in this manner until the latching projection 102 on the release lever 22 engages the annular external shoulder 54 of the spring guide, as depicted in FIG. 2. In the charged-safety-on mode, the rear section 88 of the safety cap 20 covers the release lever 22 to prevent accidental actuation of the instrument 10.

If the instrument 10 has not yet been used to perform a biopsy, it must now be loaded with a needle 24 while in the charged-safety-on mode. With the access ports 36a, 36b exposed, the biopsy instrument 10 is loaded by registering the anchor 80 on the stylet 60 with the clevis 46. The cannula mount 58, sheathing the stylet 60, is secured to the spring guide 18 by mating the thread 56 on the spring guide 18 with the thread 74 on the inner surface 72 of the collar 62 and executing a quarter-turn to secure the mating engagement of the threads.

Figure 4:
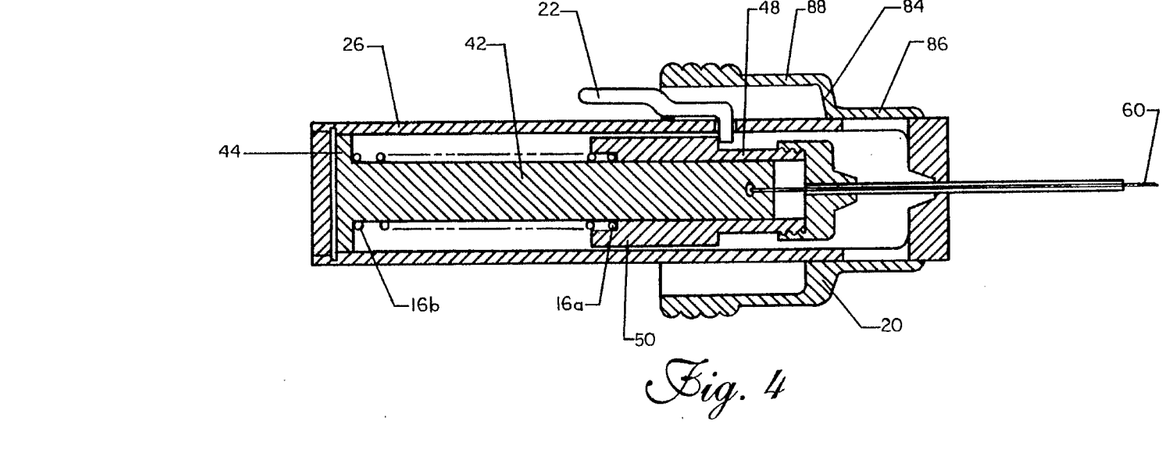
FIG. 4 is a longitudinal sectional view similar to FIG. 2 but showing the biopsy instrument of FIGS. 1 to 3 in a "charged-ready" mode.
Figure 4A:
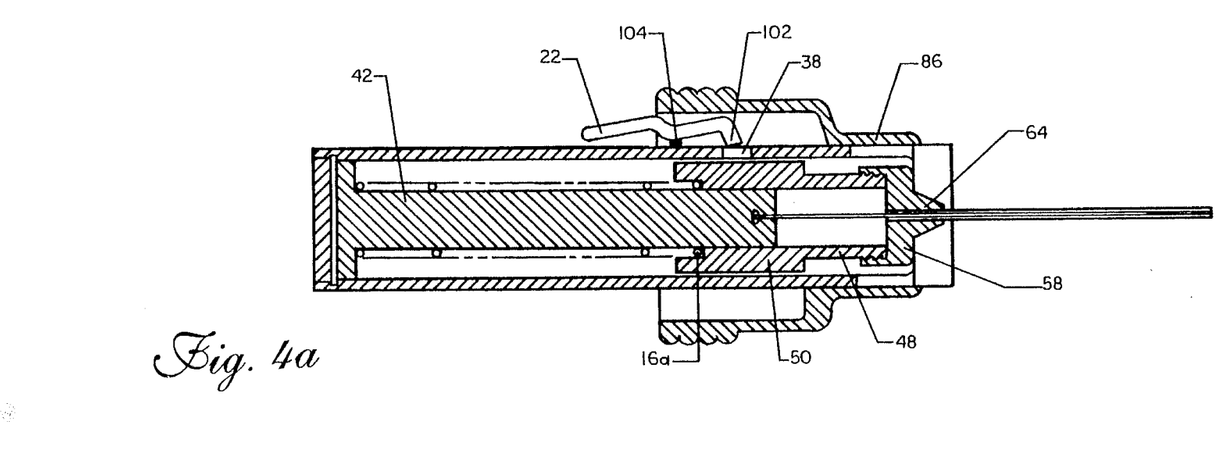
FIG. 4A is a longitudinal sectional view similar to FIG. 2 but showing the biopsy instrument of FIGS. 1 to 4 in a "discharged" mode.

To convert the instrument 10 to the charged-ready mode, best shown in FIG. 4, the safety cap 20 is moved forward until the guide pins 94 have traversed the full extent of the guide slots 40 with the safety cap covering the access ports 36a, 36b, as in the discharged mode, and exposing the release lever 22. (Alternatively the safety cap 20 may be formed with a thumb hole, not shown in the drawings, positioned over the release lever 22. In this arrangement the safety cap need not be moved forward to expose the release lever 22 but rather the release lever may be depressed, as described below, by applying sufficient force to the area of the thumb hole to overcome the natural resilience of the material of construction).

The biopsy instrument 10 is now ready for use. To obtain a biopsy, the location of the tissue to be sampled is located by one or more of a variety of methods, such as fluoroscopy, sonography, computed tomography, magnetic resonance imaging, or palpation. With the instrument 10 in the charged-safety-on-mode, the needle 24 is positioned in the tissue to be biopsied. If the operator has not already done so, he slides the safety cap 20 forward and actuates the instrument by depressing the finger rest 96 on the release lever 22, which is flexibly welded to the outer casing 12 as described hereinabove. Manipulation of the release lever raises the latching projection 102, disengaging it from the external shoulder 54 of the spring guide 18.

When the latching projection 102 is disengaged, the stored energy of the biasing means or compressed coil spring 16 is released to drive the cannula 66 forward over the stationary stylet 60 and into the mass. (If the safety cap is formed with a thumb hole, the compressed energy of the coil spring 16 will drive both the cannula and the safety cap forward because the guide pins 94 on the safety cap will be drivingly engaged by the external shoulder 54 of the spring guide 18.) Thus, a guide means for mounting the cannula 66 to the instrument 10 for reciprocating movement relative to the stationary means, between a charged position and a discharged position, has been provided.

This movement of the cannula causes its sharpened distal end 76 to cut and isolate a sample plug or core of tissue from the mass and retain it within the hollow interior of the cannula 66. The instrument 10 is now in the discharged mode (FIG. 4A), as described hereinabove, and the instrument 10 may now be withdrawn from the patient. The biopsy sample is extracted from the cannula by returning the instrument to the charged-safety-on mode, thereby retracting the cutting cannula 66 from over the end of the stylet 60 to eject the sample.

Figure 9:
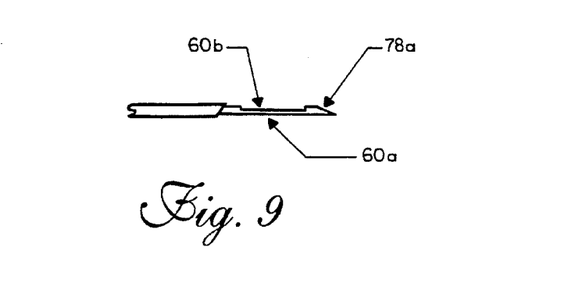
FIG. 9 is a fragmentary view of an alternative form of a stylet for a biopsy instrument according to the invention.

Because the stylet 60 is detachably affixed within the clevis 46, it may be interchanged with an alternative stylet 60a, shown fragmentarily in FIG. 9. The stylet 60a is identical to the stylet 60 except that the overall length of the stylet 60a is approximately one to two centimeters greater than that of the stylet 60, and the stylet 60a is provided with a transverse slot or sampling gap creating a tissue pocket 60b adjacent to the stylet's sharpened distal end 78a. This stylet is substantially similar to the TRU-CUT Needle marketed by Travenol Laboratories of Deerfield, Illinois. The stylet 60a may be used to perform the style of biopsy commonly referred to as the TRU-CUT method.

In performing the TRU-CUT method of biopsy using a biopsy instrument according to the present invention, the physician penetrates the mass of tissue to be sampled with the instrument 10 in the discharged mode. Because the stylet 60a is slightly longer than the stylet 60, the distal end 78a of the stylet 60a, unlike the distal end 78 of the stylet 60, projects slightly beyond the distal end of the cutting cannula 66 in the discharged mode. As the second step of the biopsy, the instrument 10 is converted to the charged-safety-on mode by retracting the cannula 66 in the manner described hereinabove. This exposes the tissue pocket 60b of the stylet 60a. In the final step of the biopsy, the physician actuates the instrument 10 by depressing the finger rest 96 of the release lever 22, which permits the energy of the compressed coil spring 16 to drive the cannula 66 forward over the stylet 60a to sever a tissue sample and retain it in the tissue pocket 60b until the instrument can be withdrawn from the patient.

FIGS. 5 to 8A illustrate an alternative embodiment of the invention in the form of a biopsy instrument 210 which is intended to be disposed of after a single use or a limited number of uses during a single procedure (perhaps three to five), whereas the embodiment illustrated in FIGS. 1 to 4A, excluding the needle 24, is suitable to be reused indefinitely. There are small differences between the two embodiments, but basic structure is quite similar in both, and their principles of operation are virtually identical. The following description is directed principally but not exclusively to the differences.

In FIGS. 5 to 8, reference numerals are greater by 200 than the respective reference numerals which identify identical or analogous elements or features depicted in FIGS. 1 to 4A. Thus, referring particularly to FIGS. 5 and 5A, an automated biopsy instrument 210 comprises an outer casing 212, an inner support rod 214, a coil spring 216, a biopsy spring guide 218, a safety cap 220, a release lever 222, and a needle 224.

In this embodiment, the cylindrical tube 226 is preferably formed of materials such as polycarbonate, delrin, nylon, polyethylene, polyvinyl chloride, acrylic, or acrylonitrile-butadiene-styrene, and is open at its forward end 232 and closed at its rear end 228 by an end wall 230 formed integrally therewith. A circular cap 231 snap-fits over the tube 226 to close the open forward end 232. A cylindrical depression 234a (FIG. 6) is formed about the center of the interior face of the cap 231. An axial bore 234 through the center of the cap communicates with the depression 234a.

Figure 5:
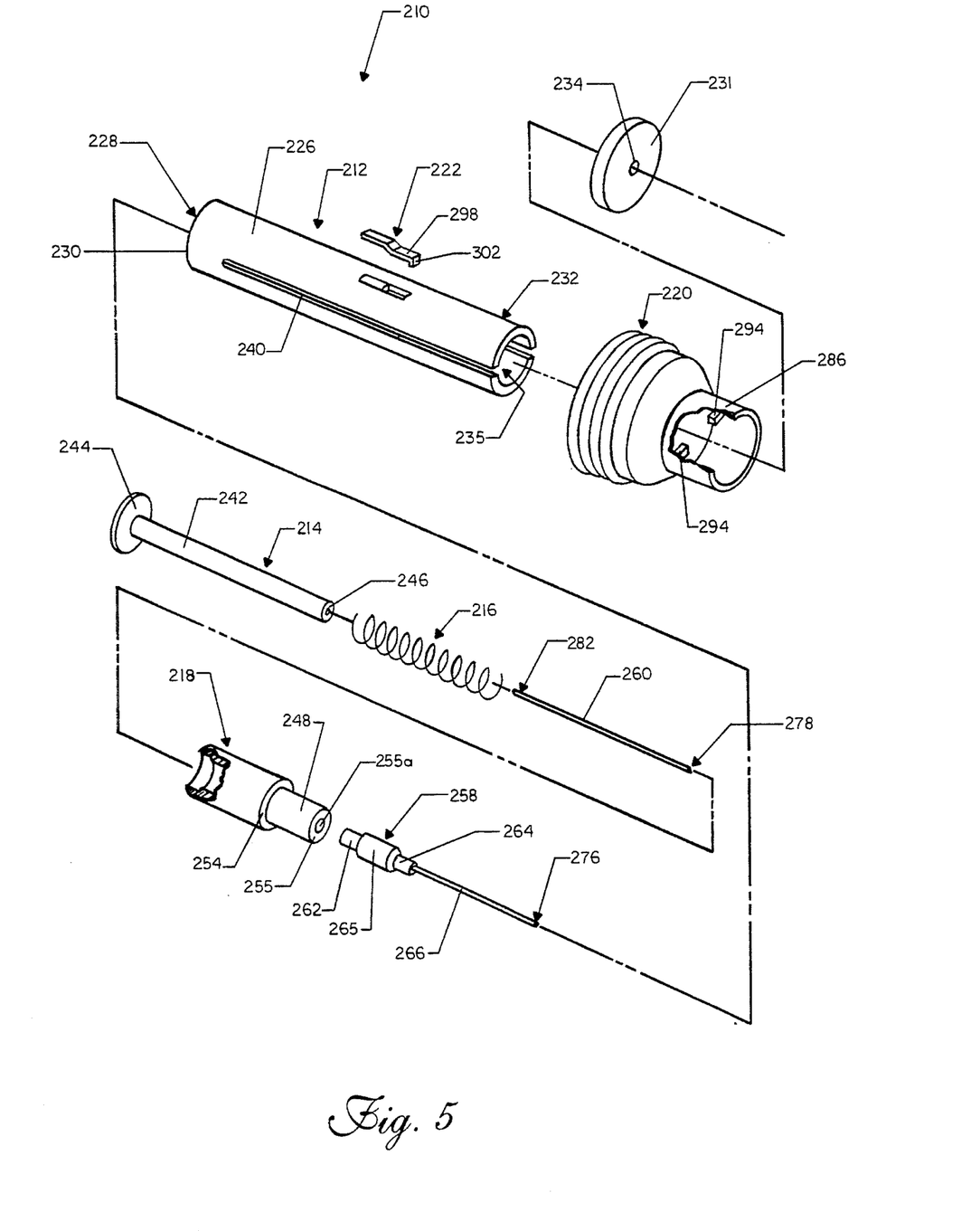
FIG. 5 is an exploded perspective view similar to FIG. 1 but showing a biopsy instrument comprising an alternative embodiment of the invention.
Figure 5A:
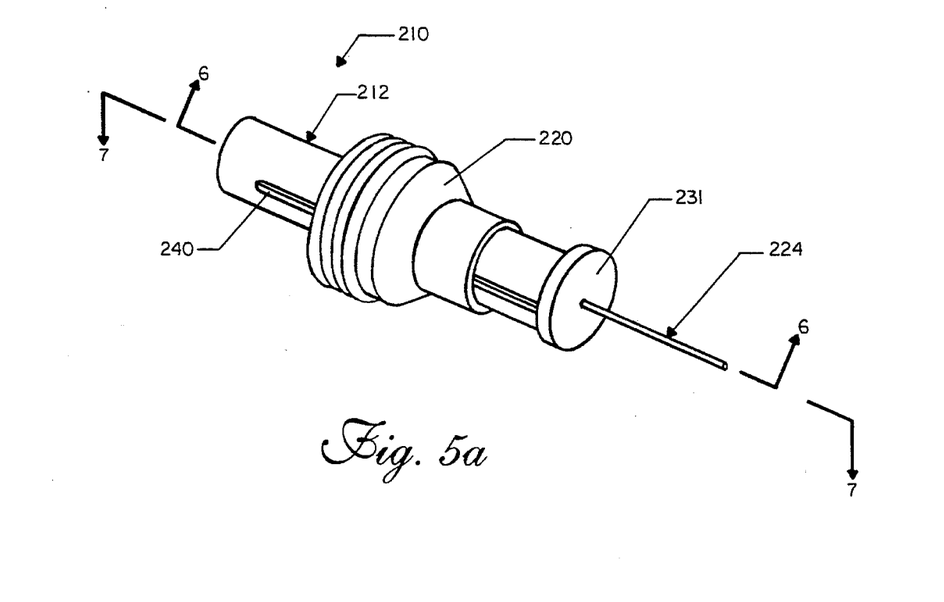
FIG. 5A is a perspective view of the biopsy instrument of FIG. 5 in a fully assembled condition.
Figure 6:
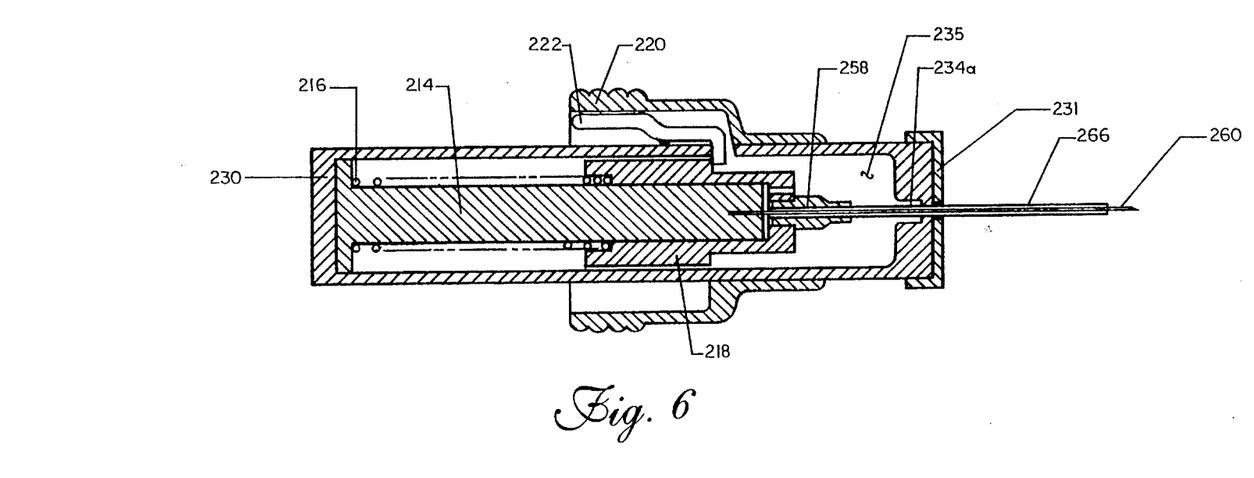
FIG. 6 is a longitudinal sectional view taken along line 6—6 of FIG. 5A and showing the biopsy instrument of FIGS. 5 and 5A in a "charged-safety-on" mode.

Also in this embodiment, the longitudinal guide slots 240 extend from the forward end 232 of the tube 226 toward the rear end 228, a recess 246 is formed in the distal end of the internal support rod 214, and the forward cylinder 248 is formed with an end wall 255 pierced by a bore 255a.

The cannula mount 258 comprises a narrow base 262, a narrow cylindrical head 264 and a midsection 265 integrally joining the base and the head. The base 262, the head 264, and the midsection 265 are axially bored to receive the cutting cannula 266, which may there be secured by means of adhesive (not shown) and which comprises a hollow cylindrical tube beveled at its distal end 276 to an appropriate angle (the particular angle depending on the style of cannula employed) and sharpened about the circumference of the distal end.

The mounting section 298 of the release lever 222 is flexibly solvent-bonded to the outer casing 212 at 304.

Assembly of instrument 210 is quite similar to assembly of instrument 10, as described hereinabove. However, in this instance, the proximal end 282 of the stylet 262 is adhesively bonded within the recess 246, and the base 262 of the cannula mount 258 is similarly secured within the bore 255a.

In any event, the internal support rod 214, the coil spring 216, the spring guide 218, and the needle 224 are telescopically received within the safety cap 220 and the outer casing 212, the guide pins 294 being received in the guide slots 240, and the cutting cannula 266 and the stylet 260 being received in the axial bore 234. The safety cap 220 is now slidable over the outer casing 212, the extent of forward movement being limited by the cap 231 which is applied to the tube 226 to close the forward end 232 thereof as well as the open ends of the guide slots 240.

Like the instrument 10, the assembled biopsy instrument 210 is operated in a discharged mode, a charged-safety-on mode, and a charged-ready mode. In the discharged mode (FIG. 8A), the safety cap 220 is positioned near the forward end 232 of the tube 226 in engagement with the cap 231. The spring guide 218 is also disposed near the forward end of the tube 226 with the cylindrical head 264 of the cannula mount 258 resting within the complementary cylindrical depression 234a.

Figure 7:
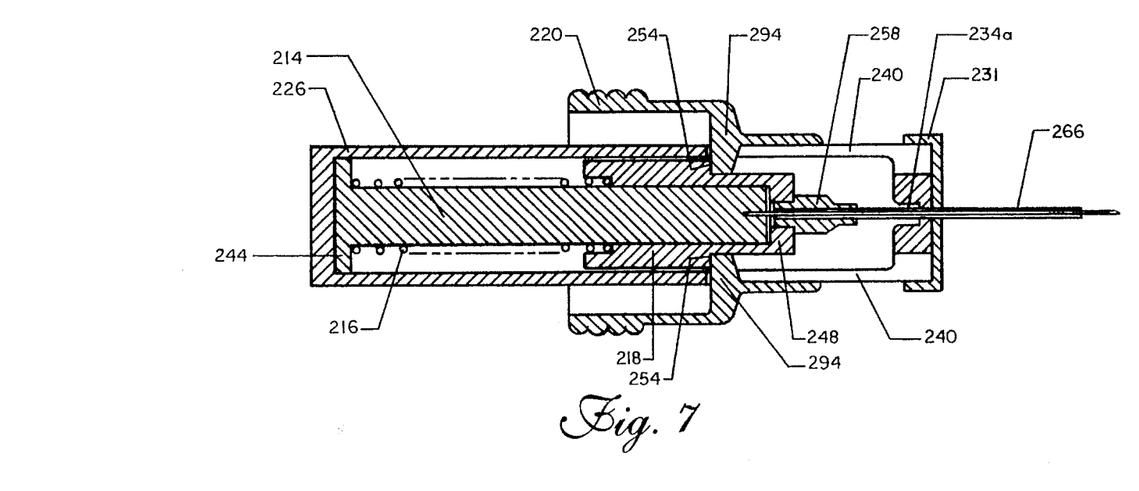
FIG. 7 is a longitudinal sectional view of the biopsy instrument of FIGS. 5, 5A and 6, taken along line 7—7 of FIG. 5A.
Figure 8:
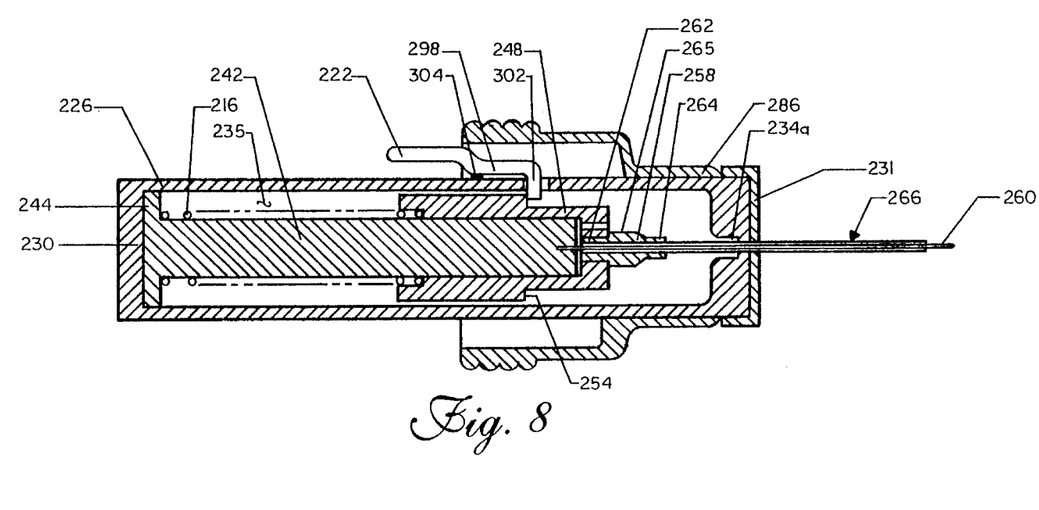
FIG. 8 is a longitudinal sectional view similar to FIG. 6 but showing the biopsy instrument of FIGS. 5 to 7 in a "charged-ready" mode.
Figure 8A:
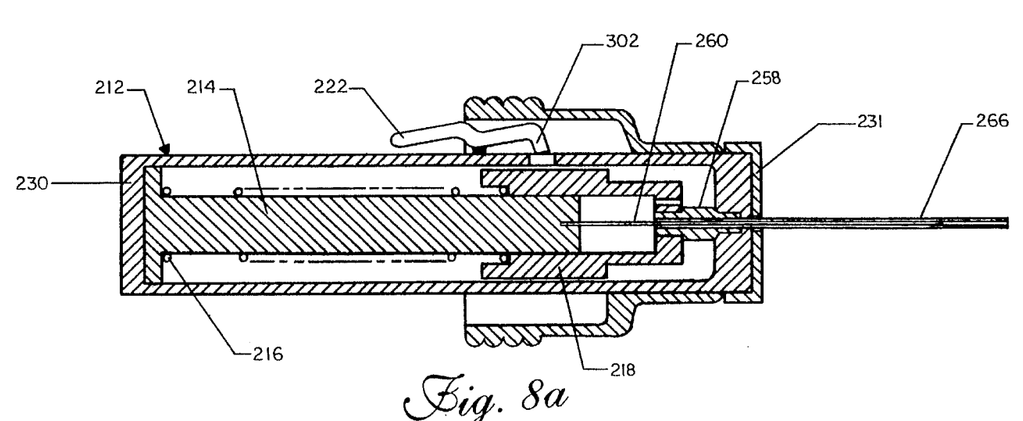
FIG. 8A is a longitudinal sectional view similar to FIG. 6 but showing the biopsy instrument of FIGS. 5 to 8 in a "discharged" mode.

The instrument 210 is converted to the charged-safety-on mode (FIG. 6) by retracting the safety cap 220 toward the rear end 228 of the outer casing 212, causing the guide pins 294 to engage the external shoulder 254 of the spring guide 218 and thus retract the spring guide toward the base 244 of the support rod 214 and compress the spring 216 (FIG. 7). The cannula 266 is simultaneously retracted to expose the distal end 278 of the stylet 260, both the stylet 260 and the support rod 214 remaining stationary, and the latching projection 302 of the release lever 222 engages the external shoulder 254 of the biopsy spring guide 218. In the charged-safety-on mode, the rear section 288 of the safety cap 220 conceals the release lever 222 to prevent accidental actuation of the biopsy instrument 210.

In converting to the charged-ready mode (FIG. 8), the safety cap 220 is slid forward into engagement with the cap 231, as in the discharged position, thereby exposing the release lever 222. The instrument 210 is now ready to be used to obtain a tissue sample in precisely the same procedure described above in connection with instrument 10 (and alternatively, the safety cap 220 may be formed with a thumb hole as described hereinabove in connection with the embodiment of FIGS. 1 to 4A). Also similar to the embodiment of FIGS. 1 to 4A, the instrument 210 may be provided with the stylet 60a, shown fragmentarily in FIG. 9, to replace the stylet 260. In the event the stylet 260 is replaced by the stylet 60a, the distal end 78a of the stylet 60a projects slightly beyond the distal end of the cannula 266 in the discharged mode, as described hereinabove.

The materials from which certain biopsy instruments according to the invention are constructed may be selected so that the instruments will be suitable for use in conjunction with magnetic resonance imaging (MRI), a medical examination technique which requires the use of instruments comprised entirely of non-ferromagnetic materials. Thus, the stylets 60 and 260 and the cutting cannulas 66 and 266, which are otherwise preferably formed of a suitable grade of stainless steel, would be replaced by stylets and cutting cannulas formed of nonferromagnetic metals typically having a high nickel content. The coil spring 16 or 216, also normally formed of steel, would be replaced by a spring formed from an alternative material having appropriate resilience and shape-retention characteristics, such as a nonferromagnetic metal having a high nickel content or the synthetic resinous material marketed by E. I. du Pont de Nemours & Co. of Wilmington, Del. under the name Hytrel.

Each of the embodiments disclosed herein may be used in conjunction with an outer guide cannula (not shown in the drawings) for performing multiple, successive biopsies on the same patient, although it should be understood that the outer guide cannula is not necessary for practicing the invention. The outer guide cannula is an elongated narrow cylindrical tube open at both ends and telescopically receivable over the needle 24, 224. It is inserted in the incision made in the tissue mass during the biopsy. If a subsequent biopsy of the same region of tissue is called for, the outer guide cannula may be allowed to remain in place in the incision when the biopsy instrument is removed to retrieve the tissue sample from the previous biopsy. To perform subsequent biopsies, the instrument is used as described hereinabove but the needle is inserted into the outer guide cannula to be conducted thereby to the correct location to perform each subsequent biopsy. This eliminates any need to leave the entire instrument projecting from the body of a patient while the tissue sample is retrieved, as must be done in such procedures when using certain known biopsy instruments from which the stylet must be removed in order to retrieve the sample.

Under either of the styles of biopsy and using either of the embodiments described hereinabove, an easily manipulated and manually compatible instrument 10, 210 is provided. The outer casing 12, 212 is of a size, shape and weight such that it can be readily held and gripped by a single hand. Further, the instrument 10, 210 is easily converted from the discharged to the charged mode by retracting the safety cap 20, 220 and the spring guide 18, 218. The pair of guide pins 94, 294 equitably distribute the force of retraction about the circumference of the annular external shoulder 54, 254 of the spring guide 218 thereby enabling the physician to readily charge the instrument. The safety cap 20, 220 provides an important degree of protection for the patient. The physician must manually advance the safety cap 20, 220 forward to expose the release lever 22, 222 or, alternatively, must supply sufficient force to the area defining the thumb hole to overcome the natural resilience of the material comprising the safety cap to depress the release lever 22, 222. In either event, the likelihood that the instrument 10, 210 may be accidentally actuated has been substantially reduced. The compact size and shape of the instrument 10, 210 affords the physician great control over the operation and manipulation of the same. Thus, the patient is less likely to sustain serious injury which could result from unwanted instrument movement or torque.

FIGS. 10 to 13 illustrate a further embodiment of the invention in the form of a sealed biopsy instrument 410 which is intended to aid in the retention of a core biopsy specimen by creating a vacuum within the biopsy instrument 310. During withdrawal of the cannula from the patient and when taking a core biopsy specimen, the specimen may be accidentally lost or removed from the cannula by the specimen falling out of the cannula or drawn out of the cannula if the specimen is not completely severed from the mass. There are small differences between this embodiment and the two previously described embodiments, but the basic structure is quite similar in both, and their principles of operation are virtually identical. The following description is directed principally, but not exclusively, to the differences.

In FIGS. 10 to 13, reference numerals are greater by 400 than the respective reference numerals which identify identical or analogous elements or features depicted in FIGS. 1 to 4a. Thus, referring particularly to FIGS. 10 and 10a, an automated biopsy instrument 410 comprises an outer casing 412, an inner support rod 414, a coil spring 416, a biopsy spring guide 418, a safety cap 420, a release lever 422, and a needle 424.

Figure 10:
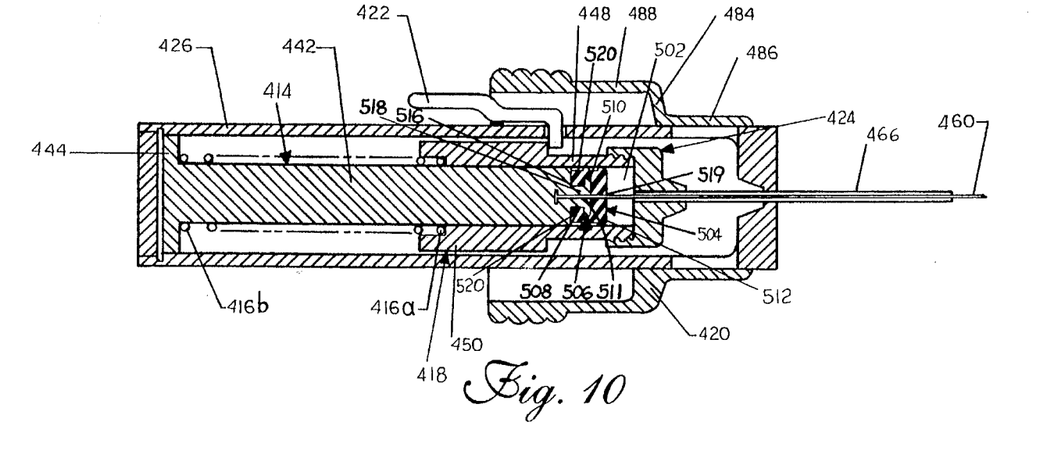
FIG. 10 is a longitudinal sectional view identical to FIG. 4 but showing an alternative embodiment of the inner support rod.

A chamber 502 is defined by the inner support rod 414, biopsy spring guide 418, and needle 424 when the biopsy instrument 410 is assembled. The chamber 502 is open to the atmosphere through the hollow cannula 466 and the clearance between the inner support rod 414 and the biopsy spring guide 418.

Figure 11:
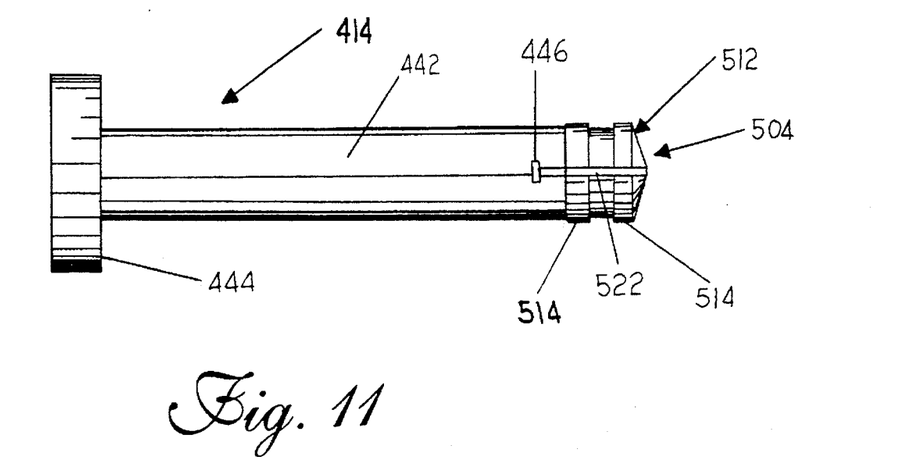
FIG. 11 is a top view of the inner support rod shown in FIGS. 10 and 10A.

The principal difference between the biopsy instrument 410 and the biopsy instruments 10 and 210 is the construction of the support rod 414. FIGS. 10 to 11 illustrate the support rod 414 with a sealing means 504, which forms a seal between the inner support rod 414 and the biopsy spring guide 418 to seal the chamber 502.

FIGS. 10 to 11 illustrate a first embodiment of the sealing means 504. In this embodiment, the end of the inner support rod 414 adjacent the clevis 446 have a T-shaped retainer 506 comprising a stem 508 and a head 510 in which is a stylet groove 511 (FIG. 11), which is aligned with the clevis 446. The T-shaped retainer 506 is adapted to receive an elastomeric sealing member, such as elastomeric cap 512. Preferably, the elastomeric cap 512 has at least two sealing ribs 514 for engaging the inner surface of the biopsy spring guide 418 to form a seal between the biopsy spring guide 418 and the inner support rod 414. However, an elastomeric cap 512 without any sealing ribs 514 would also provide a sufficient seal.

The elastomeric cap 512 comprises an inner cavity 516, which has, at one end, an annular rib 520, defining an opening 518 for receiving the T-shaped retainer 506, and, at the other end, an opening 519 for receiving the stylet 460. The elastomeric cap 512 is mounted to the T-shaped retainer 506 by inserting the head 510 of the T-shaped retainer 506 into the cavity 516 of the elastomeric cap 512 so that the annular rib 520 is stretched over the head 510 and encircles the stem 508. In this position, the annular rib 520 of the elastomeric cap 512 is in abutting relationship with the head 510 to prevent the removal of the elastomeric cap 512 from the T-shaped retainer 506.

Figure 12:
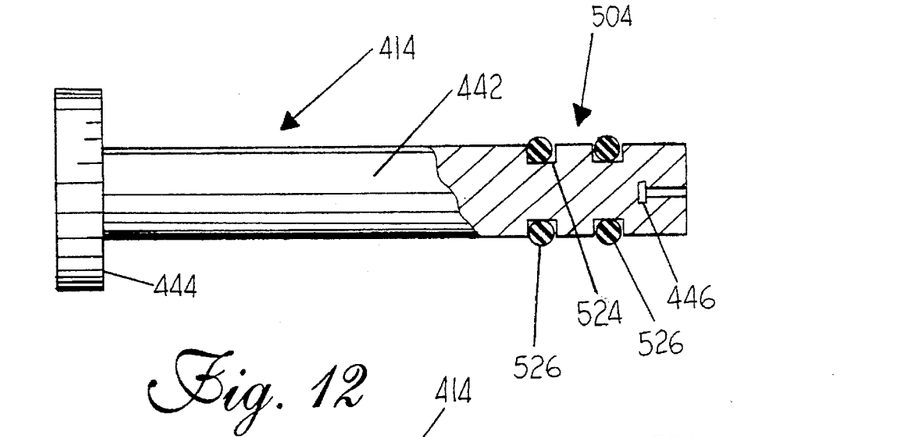
FIG. 12 is a side view of another alternative embodiment of the inner support rod shown in FIGS. 10–11.

Referring to FIG. 12, if the elastomeric cap 512 is used in combination with a reusable biopsy instrument 410 (FIGS. 10 to 11), the elastomeric cap 512 will have a slit 522 (FIG. 11), which is positioned to align with the groove 511 in the T-shaped retainer 506 and the clevis 446 so that the stylet 460 can be mounted in the clevis 446. The slit 522 in the elastomeric cap 512 does not impair the seal between the biopsy spring guide 418 and the inner support rod 414 because the elastomeric cap 512 is sufficiently compressed to fill in the slit 522 during operation of the biopsy instrument 410. If a disposable biopsy instrument 410 is used, the elastomeric cap 512 will not have a slit 522.

When the biopsy instrument 410 is used to take a core biopsy specimen, the biopsy instrument 410 is first charged as previously described and as shown in FIG. 10. As the biopsy instrument 410 is placed in the charged position, the volume of the chamber 502 is at its minimum because the biopsy spring guide 418 and the needle 424 are moved toward the base 444 of the support rod 414. When charged, the stylet 460 extends slightly beyond the distal end of the cannula 466 to aid the insertion of the biopsy instrument 410 into the patient.

Figure 10A:
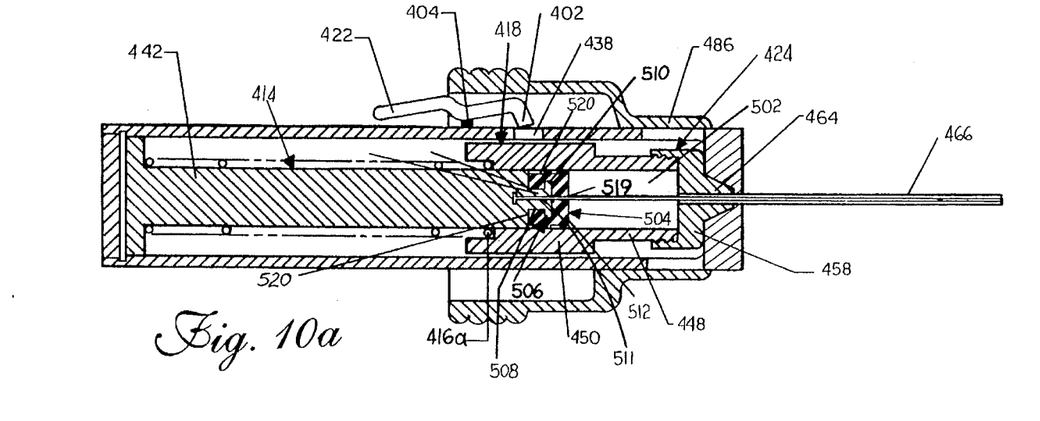
FIG. 10A is a longitudinal sectional view identical to FIG. 4a but showing an alternative embodiment of the inner support rod.

Once the biopsy instrument 410 is inserted into the patient at the desired position, the biopsy instrument 410 is discharged by pressing the release lever 422, resulting in the biopsy spring guide 418, cannula mount 458 and cannula 466 being propelled forward by the spring 416 to sever a core biopsy specimen from the patient. As the biopsy spring guide 418 and the needle 424 move forward with respect to the inner support rod 414, the volume of the chamber 502 is increased, until it reaches its maximum volume when the biopsy instrument is in the fully discharged position (FIG. 10a). During the discharging of the biopsy instrument 410, the end of the cannula is sealed by the core biopsy specimen within the cannula 466. Thus, the sealing means 504 and the biopsy specimen retained within the cannula completely seal the chamber 502, creating a vacuum within the chamber 502 that extends down the cannula 466 to the biopsy specimen. The suction of the vacuum on the biopsy specimen helps to retain the biopsy specimen within the cannula 466. To remove the biopsy specimen from the cannula 466, the biopsy instrument 410 is charged once again so that the stylet pushes the biopsy specimen out of the cannula.

Figure 13:
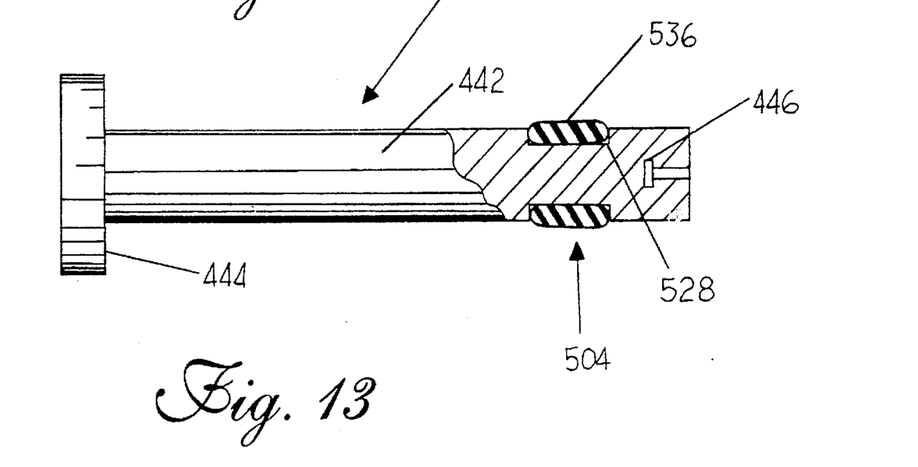
FIG. 13 is a side view of a further alternative embodiment of the inner support rod shown in FIGS. 10–11.

FIGS. 12 and 13 illustrate alternative embodiments of the sealing means 504. Referring to FIG. 12, the inner support rod 414 has one or more annular notches or grooves 524, which receive elastomeric sealing members, such as O-rings 526. The O-rings 526 form the seal between the inner support rod 414 and the biopsy spring guide 418. Referring to FIG. 13, a single annular groove 528 is formed in the inner support rod 414 and receives an elastomeric sealing member, such as elastomeric sleeve 530. The elastomeric sleeve forms the seal between the inner support rod 414 and the biopsy spring guide 418. Preferably, the O-rings 526 and the elastomeric sleeve 530 are disposed behind the clevis 446 of the inner support rod 414 so there is no need for either of the O-rings 526 and elastomeric sleeve 530 to have a slit through which the stylet would pass to mount within the clevis 446, as is required in the first embodiment of the sealing means 504. Therefore, the O-rings 526 and elastomeric sleeve 530 have identical construction for both a reusable and disposable biopsy instrument 410, unlike the elastomeric cap 512.

Figure 14:
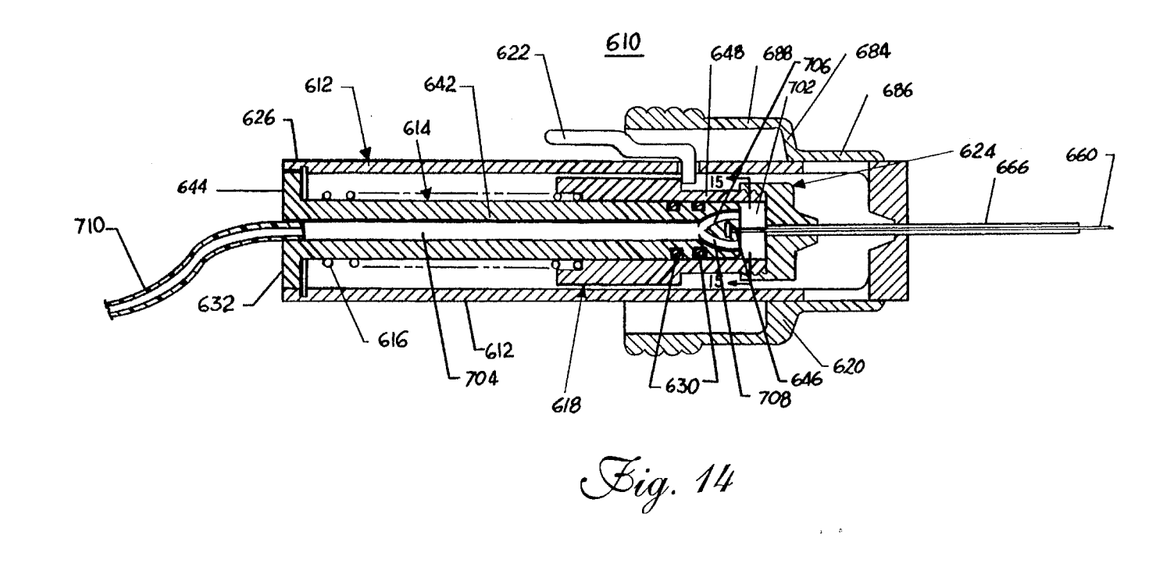
FIG. 14 is a longitudinal sectional view similar to FIG. 10 but showing a further alternative embodiment of the biopsy instrument according to the invention.
Figure 15:
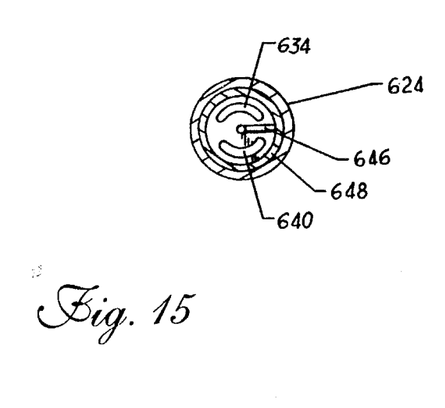
FIG. 15 is a sectional view taken along line 15—15 of FIG. 14.

FIGS. 14 and 15 illustrate a further embodiment of the invention in the form of a sealed biopsy instrument 600, which is similar to the embodiment illustrated in FIGS. 1 to 13 and especially the forms illustrated in FIGS. 10 to 13 in that both embodiments are intended to aid in the retention of a core biopsy specimen by creating a vacuum within the biopsy instrument. There are small differences between this embodiment and the modifications depicted in FIGS. 10 to 13, but the basic structure is quite similar in both and their principals of operation are virtually identical. The following description is directed principally, but not exclusively, to the differences.

In FIGS. 14 and 15, reference numerals are greater by 600 than the respective reference numerals which identify identical or analogous elements or features depicted in FIGS. 1 to 4A. Thus, referring particularly to FIGS. 14 and 15, an automated biopsy instrument 610 comprises an outer casing 612, an inner support rod 614, a coil spring 616, a biopsy spring guide 618, a safety cap 620, a release lever 622, and a needle assembly 624. A chamber 702 is defined by the inner support rod 614, biopsy spring guide 618, and needle 624 when the biopsy instrument 610 is assembled.

The principal difference between the biopsy instrument 610 and the biopsy instruments 10, 210, and 410 is the construction of the support rod 614. The support rod 614 is similar to the support rod 414 in that it has sealing means 630, which form a seal between the inner support rod 614 and the biopsy spring guide 618. The sealing means 630 are illustrated as a pair of O-rings. However, any of these sealing means disclosed in FIGS. 10 to 13 can be used in place of the O-rings.

Unlike the previously described support rods, the support rod 614 has an end plate 644, which closes the corresponding end of the casing 612 and from which extends a hollow rod 642 defining a channel 704 throughout the length of the rod 614. The end of the rod 614 opposite from the end plate 644 is provided with a clevis 646 formed therein and adapted to receive the end of a stylet 660. More particularly, the channel 704 begins at the end plate 644 and maintains a substantially constant diameter until it approaches the end of the hollow rod 642 near the clevis 646. The channel is then divided into an upper portion 706 and a lower portion 708. The upper and lower portions 706, 708 are access openings connecting the channel 704 to the chamber 702. As can be seen in FIG. 15, the upper and lower channel portions 706 and 708 are semicircular and situated on diametrically opposite sides of the clevis 646. The upper and lower portions 706 and 708 are preferably large enough to provide fluid communication between the channel 704 and the chamber 702, but are nevertheless small enough that the hollow rod 642 will have a sufficient amount of material for the clevis 646 to support the stylet 660.

Although the channel 704 is shown as being divided into upper and lower portions 638 and 640, it is within the scope of the invention for the channel to be provided with other access openings to the chamber 702. Such other access openings may be in addition to or substituted for the upper and lower channel portions 706 and 708, and may comprise one or more apertures of varying shapes connecting the channel 704 to the chamber 702. Similarly, the support rod near the clevis might be formed with a reduced diameter and the access openings might extend radially outwardly to the sides of the reduced diameter portion instead of to the end of the hollow rod 642. The only limitation on the access openings is that they must provide fluid communication between the channel 704 and the chamber 702.

The biopsy actuator 610 operates identically in the manner of the biopsy instrument 410, as described above, except than an low-pressure device such as an auxiliary vacuum, auxiliary vacuum device (not shown) is coupled to the channel 704 of the biopsy instrument 610 by any suitable device, such as hose, which is press-fit within the channel 704 at the end thereof at the end plate 644 to provide an additional vacuum within the chamber 626 during the taking of a core biopsy specimen. When the auxiliary vacuum device is not coupled to the channel 704 of the biopsy instrument 610, a cap can be applied to the rearward end of channel 704 to allow for operation of the device without an auxiliary vacuum device. A brief description of the operation of the biopsy instrument 610 follows.

When the biopsy instrument 610 is used to take a core biopsy specimen, it is first charged as previously described and as shown in FIG. 10. As the biopsy instrument is placed in the charged position, the volume of the chamber 702 is at its minimum. In the charged position, the stylet 660 extends slightly beyond the distal end of the cannula 666 to aid insertion into the tissue of the patient.

After insertion, the biopsy instrument 610 is discharged by pressing the release lever 622, permitting the cannula 666 to be driven forward and beyond the end of the stylet 660 to sever a core biopsy specimen from the patient and retain it within the cannula. As the cannula is driven forward, the distance between the needle assembly 624 and the end of the inner support rod 614 is increased to increase the volume of the chamber 702, which, as described previously, induces a low-pressure area or vacuum within the cannula 666. The suction provided by the low pressure acting on the biopsy specimen helps to retain the specimen within the cannula. As soon as the biopsy actuator 610 is in the discharged position and the cannula completes its forward movement, the auxiliary vacuum device is energized to enhance the vacuum within the chamber 626 and thereby further aid in retaining the biopsy specimen within the cannula. The auxiliary vacuum device remains actuated until the biopsy instrument 610 is removed from the patient, whereupon the auxiliary vacuum device is de-energized and the core biopsy specimen is removed from the cannula by moving the biopsy instrument 610 into the charged position to cause the stylet 660 to expel the core biopsy specimen from the cannula.

Alternatively, it is within the scope of the invention for the auxiliary vacuum device to be energized throughout the entire procedure. In such a case, it is necessary only that the spring 616 have sufficient force to overcome the suction force created by the auxiliary vacuum device so that the low pressure will not prevent the biopsy instrument 610 from being discharged.

While the invention has been particularly described in connection with certain specific embodiments thereof, it is to be understood that this is by way of illustration and not of limitation, and the scope of the appended claims should be construed as broadly as the prior art will permit. For example, although the vacuum created by the sealed chamber is described herein with respect to the core biopsy specimen method, it is within the scope of the invention to employ the vacuum in performing the TRU-CUT® method described above.

What is claimed is:

1. An apparatus for acquiring a biopsy specimen comprising:
   a biopsy actuator;
   a cannula having a predetermined inner diameter, a distal end for insertion in the body of a patient and an opposing proximal end attached to the biopsy actuator;
   a stylet attached to the biopsy actuator having a predetermined outer diameter commensurate with the inner diameter of the cannula and being receivable within the cannula by way of the proximal end of the cannula; and
   means for rapidly advancing the distal end of the cannula beyond the distal end of the stylet to acquire a biopsy specimen;
   the biopsy actuator comprising a casing enclosing a sealed chamber in fluid communication with the cannula for creating a low-pressure area in the sealed chamber and the cannula when the cannula is advanced during acquisition of a biopsy specimen;
   the biopsy actuator further comprising a coupling for connection of the sealed chamber with a low-pressure device in fluid communication therewith.

2. An apparatus according to claim 1 wherein the biopsy actuator further comprises a stylet support, and a cannula support cooperating therewith to define the sealed chamber.

3. An apparatus according to claim 2 wherein the biopsy actuator further comprises means forming a substantially fluid-tight seal between the stylet support and the cannula support.

4. An apparatus according to claim 3 wherein the seal-forming means comprises an elastomeric sealing member.

5. An apparatus according to claim 4 wherein the stylet support is provided with a retaining member and the elastomeric sealing member comprises an elastomeric cap mounted to the retaining member.

6. An apparatus according to claim 4 wherein the stylet support comprises a groove formed therein and the elastomeric sealing member comprises an elastomeric O-ring disposed in the groove.

7. An apparatus according to claim 4 wherein the stylet support comprises a groove formed therein and the elastomeric sealing member is an elastomeric sleeve disposed within the groove.

8. An apparatus according to claim 2 wherein the stylet support comprises a hollow rod defining a channel extending through the stylet support, one end of the channel forming the coupling and the other end of the channel being fluidly connected to the sealed chamber.

9. An apparatus according to claim 8 wherein the channel has at least one access opening fluidly connecting the channel to the sealed chamber.

10. An apparatus according to claim 9 wherein the access opening extends from the channel to a lateral portion of the stylet support.

11. An apparatus according to claim 9 wherein the stylet support further comprises a clevis for mounting the stylet and the at least one access opening is disposed away from the clevis.

12. An apparatus according to claim 8 wherein the stylet support further comprises an end plate mounted to the one end of the stylet support and sized to close an end of the casing.

13. An apparatus according to claim 12 wherein the end plate forms the coupling.

14. An apparatus according to claim 13 wherein the coupling is a hose having one end press-fit within the channel and the other end adapted to mount to the low-pressure device.

15. An apparatus for acquiring a biopsy specimen comprising:
   a biopsy actuator comprising a casing;
   a cannula having a predetermined inner diameter, a distal end for insertion in the body of a patient and an opposing proximal end attached to the biopsy actuator;
   a stylet attached to the biopsy actuator having a predetermined outer diameter commensurate with the inner diameter of the cannula and being receivable within the outer cannula by way of the proximal end of the outer cannula;
   means for rapidly advancing the distal end of the cannula beyond the distal end of the stylet means to acquire a biopsy specimen;
   the biopsy actuator comprising a casing enclosing a sealed chamber in fluid communication with the cannula for creating a low-pressure area in the sealed chamber and the cannula when the cannula is advanced during acquisition of a biopsy specimen;
   the biopsy actuator further comprising a coupling; and
   a low-pressure device mounted to the coupling whereby the low-pressure device is in fluid communication with the sealed chamber to form a low-pressure area in the sealed chamber by energizing the low-pressure device.

16. A method for taking a biopsy specimen from a mass with a biopsy instrument comprising a biopsy actuator, a cannula having a predetermined inner diameter, a distal end for insertion in the body of a patient and an opposing proximal end attached to the biopsy actuator, a stylet attached to the biopsy actuator having a predetermined outer diameter commensurate with the inner diameter of the cannula and being received within the outer cannula by way of the proximal end of the outer cannula, means for rapidly advancing the distal end of the cannula beyond the distal end of the stylet means to acquire a biopsy specimen, the biopsy actuator comprising a casing enclosing a sealed chamber in fluid communication with the cannula for creating a low-pressure area in the sealed chamber and the cannula when the cannula is advanced during acquisition of a biopsy specimen, the method comprising:

providing a low-pressure device;

coupling the low-pressure device to the sealed chamber;

inserting the biopsy actuator into the mass;

advancing the distal end of the cannula over the distal end of the stylet to sever a biopsy specimen from the mass; and withdrawing the biopsy actuator from the mass.

17. The method according to claim 16 and further comprising the step of actuating the low-pressure device to form a low pressure within the sealed chamber and the cannula prior to the step of advancing the cannula.

18. The method according to claim 16 and further comprising the step of actuating the low-pressure device to form a low pressure within the sealed chamber and the cannula after the step of advancing the cannula.

* * * * *